(12) United States Patent
Greenberg et al.

(10) Patent No.: US 7,765,009 B2
(45) Date of Patent: *Jul. 27, 2010

(54) SUB-THRESHOLD STIMULATION TO PRECONDITION NEURONS FOR SUPRA-THRESHOLD STIMULATION

(75) Inventors: Robert J. Greenberg, Los Angeles, CA (US); Matthew J. McMahon, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/924,313

(22) Filed: Oct. 25, 2007

(65) Prior Publication Data

US 2008/0046031 A1 Feb. 21, 2008

Related U.S. Application Data

(62) Division of application No. 11/523,897, filed on Sep. 19, 2006.

(60) Provisional application No. 60/718,659, filed on Sep. 19, 2005.

(51) Int. Cl.
*A61N 1/00* (2006.01)

(52) U.S. Cl. ........................................................ 607/53
(58) Field of Classification Search ................... 607/53, 607/54

See application file for complete search history.

(56) References Cited

U.S. PATENT DOCUMENTS

| | | | |
|---|---|---|---|
| 5,109,844 A | 5/1992 | de Juan, Jr. et al. | |
| 5,935,155 A | 8/1999 | Humayun et al. | |
| 6,400,989 B1 | 6/2002 | Eckmiller | |
| 6,458,157 B1 | 10/2002 | Suaning | |
| 6,505,078 B1 | 1/2003 | King et al. | |

(Continued)

OTHER PUBLICATIONS

Grill, Warren M., et al., Stimulus Waveforms for Selective Neural Stimulation; IEEE Engineering in Medicine and Biology, Jul./Aug. 1996; pp. 375-385; 0739-5175/95.

*Primary Examiner*—Scott M Getzow
(74) *Attorney, Agent, or Firm*—Scott B. Dunbar; Alessandro Steinfl

(57) ABSTRACT

In order to generate the smallest phosphenes possible, it is advantageous to selectively stimulate smaller cells. By hyperpolarizing the somas of the large cells selectively with sub-threshold anodic 'pre-pulse' stimuli (making them more difficult to stimulate) and then selectively depolarize the smaller cells one can selectively stimulate smaller cells. Alternatively, one can hyperpolarize the dendrites of the cells with larger dendritic fields by applying sub-threshold anodic currents on surrounding electrodes and then depolarizing the smaller cells in the center. Further, one can manipulate the phases of an individual biphasic wave to affect selective stimulation resulting in more focal responses. It is possible to increase resolution with the 'pre-pulse' described above. One can also effect resolution by modifying the pulse order of the cathodic and anodic phases. Further, one can isolate the effect of the phases by separating them in time (long inter-phase interval) or by making one of the phases long and low amplitude—always keeping equal total charge for the two phases. As an example, one can preferentially stimulate smaller ganglion cells by providing a longer sub-threshold anodic pulse balanced with a shorter supra-threshold cathodic pulse. Preferentially stimulating the smaller ganglion cells will allow stimulation of different brightness levels while maintaining high spatial resolution.

11 Claims, 4 Drawing Sheets

U.S. PATENT DOCUMENTS

| | | |
|---|---|---|
| 6,882,881 B1 | 4/2005 | Lesser et al. |
| 2004/0044379 A1 | 3/2004 | Holsheimer |
| 2005/0004624 A1* | 1/2005 | Gliner et al. .................. 607/54 |
| 2005/0070971 A1* | 3/2005 | Fowler et al. .................. 607/45 |
| 2006/0058857 A1* | 3/2006 | Tano et al. .................... 607/54 |
| 2006/0167528 A1 | 7/2006 | Roy et al. |

\* cited by examiner

SUB-THRESHOLD STIMULATION TO PRECONDITION NEURONS FOR SUPRA-THRESHOLD STIMULATION

CROSS REFERENCE TO RELATED APPLICATIONS

This application is a divisional application of U.S. application Ser. No. 11/523,897, filed Sep. 19, 2006, for Sub-threshold Stimulation to Precondition Neurons for Supra-threshold Stimulation, which claims the benefit of U.S. Provisional Application No. 60/718,659, "Threshold Stimulation to Precondition Neurons to Subsequent Supra-threshold Stimulation", filed Sep. 19, 2005, the disclosure of which is incorporated herein by reference. This application is related to U.S. Pat. No. 5,944,747, Method for Preferential Outer Retinal Stimulation, which is incorporated herein by reference.

GOVERNMENT RIGHTS NOTICE

This invention made with government support under grant No. R24EY12893-01, awarded by the National Institutes of Health. The government has certain rights in the invention.

FIELD OF THE INVENTION

The present invention is generally directed to neural stimulation and more specifically to an improved method of improving resolution by selectively stimulating smaller cells.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across retinal neuronal cell membranes, which can initiate retinal neuronal action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the retinal neurons, and avoid undue compression of the retinal neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated a cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

It is known that neurons respond best to change in stimuli. The retina, if continuously stimulated in a consistent manner, will slowly become less and less sensitive to the stimulus. This causes the perception of a constant visual image to gradually disappear. Those with normal vision are unable to perceive this effect because the eye constantly moves, motions called jitter or microsaccades. A normal retina has approximately 105 million light transducer cells (rods and cones), hence it requires a minute movement to change the light intensity cast upon a given light transducer.

A retinal prosthesis, according to the present invention, has two disadvantages. First, the resolution of an electrode array applied to the retina is significantly lower than the resolution of a healthy retina, requiring a greater movement to move an image from one electrode to the next electrode, as compared to one cone to the next cone. Further, a head mounted camera does not have the natural jitter or microsaccades of an eye. Therefore it is necessary to achieve the required change in another manner.

It is also known that major neural processing is done within the retina. Hence, a continuously stimulated cone will not result in a continuous signal to the brain. Ganglion and bipolar cells signal changes over space and time more readily than constant information. In a retina damaged by outer-retinal degeneration, rods and cone cannot be stimulated, since they are dead. Electrically stimulating cells further along the neural pathway bypasses the neural processing performed by the cellular layers of the inner retina. This processing must be simulated electronically to gain normal brain stimulation.

The ability to perceive a constant image, while maintaining the image contrast, is necessary to the design of a visual prosthesis.

SUMMARY OF THE INVENTION

In electrical stimulation, neurons generally have a binary effect. That is, if stimulated above threshold, it will transmit a signal to the next neuron in its neural circuit by firing an action potential. A higher charge will not elicit a larger action potential. However, increasing the amplitude of stimulation may cause the cell to fire action potentials at a higher rate or may cause more cells to fire.

In a visual prosthesis, perceived brightness can be increased by increasing the current to a stimulating electrode (whether the electrode is in the retina, optic nerve or visual cortex). This increase in current also results in a current density profile that provides supra-threshold stimulation over a greater spatial area on the retina, thereby causing more neurons to fire. However, causing neurons to fire over a lager area reduces spatial resolution. By preferentially stimulating certain types of neurons, it is possible to stimulate at different brightness levels while maintaining high spatial resolution.

Ganglion cell types with small cell bodies and dendritic fields (i.e. midget ganglion cells) underlie the perception of fine detail, so it may be advantageous to determine electrical stimulation parameters to selectively map the spatial detail to a spatial pattern of activation in these particular cells.

It is possible to selectively activate specific classes of ganglions cells (i.e. ganglion cells with smaller receptive fields can be selectively targeted). It has been shown that the relative proportion of bipolar and ganglion cells that are electrically stimulated can be controlled by manipulating the pulse width (see U.S. Pat. No. 5,944,747, Method for Preferential Outer Retinal Stimulation).

Another possibility is to use amplitude (i.e. differential cell threshold) to select cell types. Using the notion that the voltage gradient for stimulation is steeper, and therefore more effective, in polarizing cell membranes of larger cells, it is possible to selectively activate the processes or cell bodies of larger cells. It is well known that larger cells have lower thresholds and are therefore easier to selectively stimulate with low currents than smaller cells. In fact, we have studied individual ganglion cell types in normal rabbit retina and found that the large alpha retinal ganglion cells are stimulated with currents around 16 uA, while the smaller 'Local Edge Detector' retinal ganglion cells have much higher thresholds of around 51 uA when stimulating with very small conical stimulating electrodes. This data is encouraging that selective stimulation is possible, however as predicted, larger cells are easier to stimulate than smaller cells. So, in order to generate the smallest phosphenes possible, it is advantageous to selectively stimulate the smaller cells. By hyperpolarizing the somas of the large cells selectively with sub-threshold anodic 'pre-pulse' stimuli (making them more difficult to stimulate) and then selectively depolarize the smaller cells one can selectively stimulate smaller cells. Alternatively, one can hyperpolarize the dendrites of the cells with larger dendritic fields by applying sub-threshold anodic currents on surrounding electrodes and then depolarizing the smaller cells in the center. Further, one can even manipulate the phases of an individual biphasic wave to affect selective stimulation resulting in more focal responses.

The cathodic and anodic phases of the biphasic pulse can be used independently to selectively target different cell classes with smaller receptive fields. For safety reasons, the electrical pulses delivered to the retina consist of equal amount of negative (cathodic) and positive (anodic) charge. As in most other neural prosthetics, we have found thresholds in retinal cells and human subjects are generally lower for cathodic stimulation compared to anodic stimulation. Asymmetric charge-balanced biphasic stimulus waveforms can selectively activate cell bodies versus axons.

Hence, it is possible to increase resolution with the 'prepulse' described above. One can also affect resolution by modifying the pulse order of the cathodic and anodic phases. Further, one can isolate the effect of the phases by separating them in time (long inter-phase interval) or by making one of the phases long and low amplitude—always keeping equal total charge for the two phases. As an example, one can preferentially stimulate smaller ganglion cells by providing a longer sub-threshold anodic pulse balanced with a shorter supra-threshold cathodic pulse.

Alternatively, one can create the opposite effect by preconditioning neurons with sub-threshold cathodic stimulation which will preferentially stimulate larger ganglion cells. While larger cells are preferentially stimulated due to their lower threshold, it may be advantageous to preferentially stimulate these cells to more completely exclude smaller ganglion cells.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
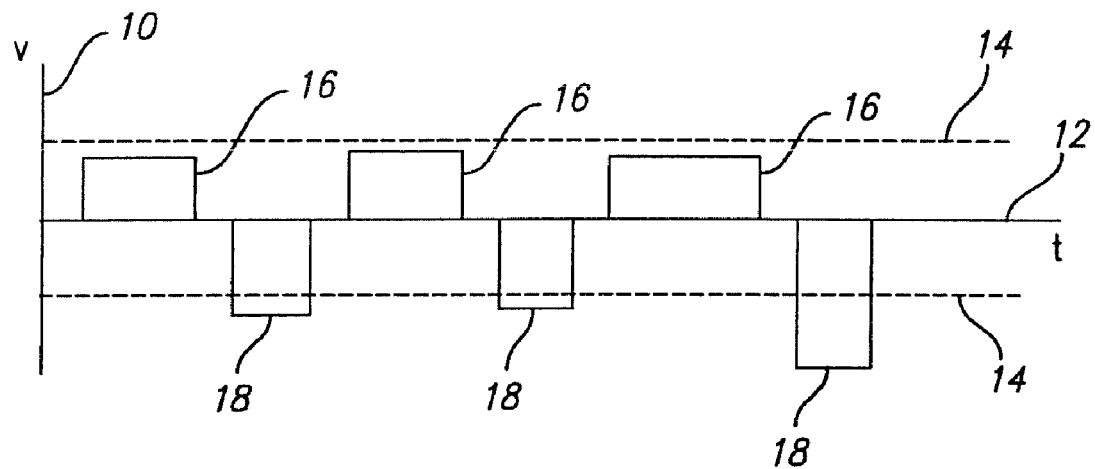
FIG. 1 depicts stimulation patterns for selectively stimulating smaller cells.

FIG. 1, depicts the preferred method of stimulation for selectively stimulating smaller cells and smaller dendritic fields. The vertical axis 10 is voltage and the horizontal axis 12 is time. Dashed lines 14 show the threshold for firing. Stimulation begins with a sub-threshold anodic pulse 16 which hyperpolarizes larger cells and larger dendritic fields. This is followed by a supra-threshold cathodic pulse 18, which selectively stimulates smaller cells and smaller dendritic fields. In order to avoid damage to both tissue and electrodes, the stimulation must be charged balanced. Hence, the sub-threshold anodic pulse 16 must be longer duration than the supra-threshold cathodic pulse 18. Since perceived brightness is proportional to the amplitude of the supra-threshold cathodic pulse 18, the sub-threshold anodic pulse 16 must vary in duration to compensate for the amplitude of the supra-threshold cathodic pulse 18.

Figure 2:
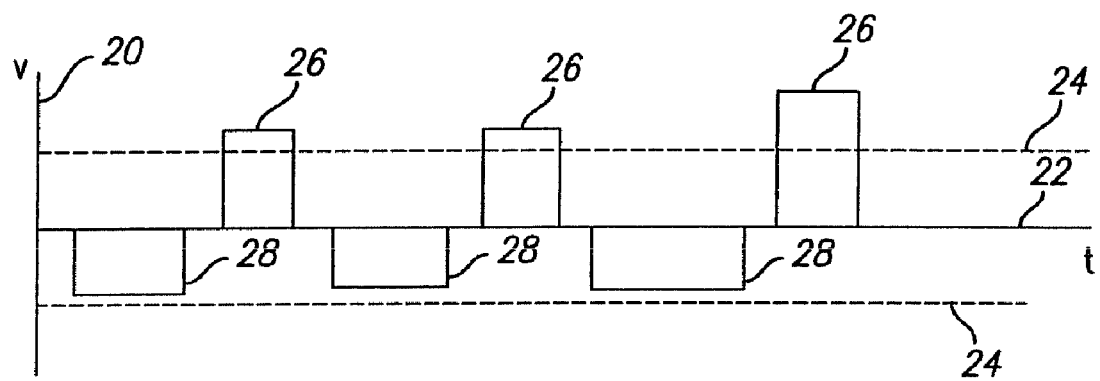
FIG. 2 depicts stimulation patterns for selectively stimulating larger cell.

FIG. 2, depicts an alternate method of stimulation for selectively stimulating larger cells and larger dendritic fields. The vertical axis 20 is voltage and the horizontal axis 22 is time. Dashed lines 24 show the threshold for firing. Stimulation begins with a sub-threshold cathodic pulse 26 which hyperpolarizes smaller cells and smaller dendritic fields. This is followed by a supra-threshold anodic pulse 28, which selectively stimulates larger cells and larger dendritic fields.

Figure 3:
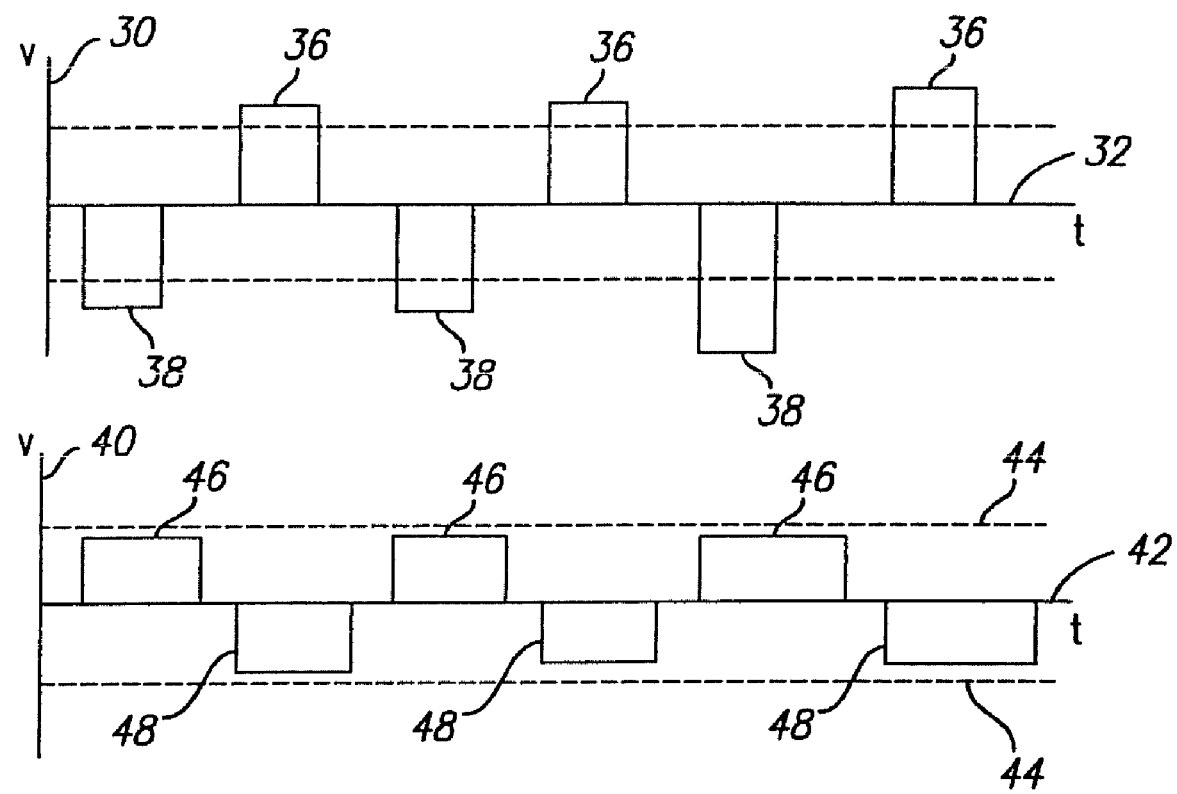
FIG. 3 depicts stimulation patterns for selectively stimulating smaller cells using multiple electrodes.

FIG. 3, depicts an alternate method of stimulation for selectively stimulating smaller cells using multiple electrodes. FIG. 3, depicts two charts where the vertical axis 30 is voltage for the stimulating electrode and the vertical axis 40 is voltage for the surrounding electrodes, and the horizontal axes 32 and 42 are time. Dashed lines 34 and 44 show the threshold for firing. Stimulation begins with a simultaneous sub-threshold anodic pulse 46 on the surrounding electrodes which hyperpolarizes larger cells and larger dendritic fields with a supra-threshold cathodic pulse 38 on the stimulating electrode, which selectively stimulates smaller cells and smaller dendritic fields. This is followed by a sub-threshold cathodic pulse 48 on the surrounding electrodes with a supra-threshold anodic pulse on the stimulating electrode 36. Note that stimulation is charged balanced on each electrode as well as equal and opposite between stimulating and surrounding electrodes.

Figure 4:
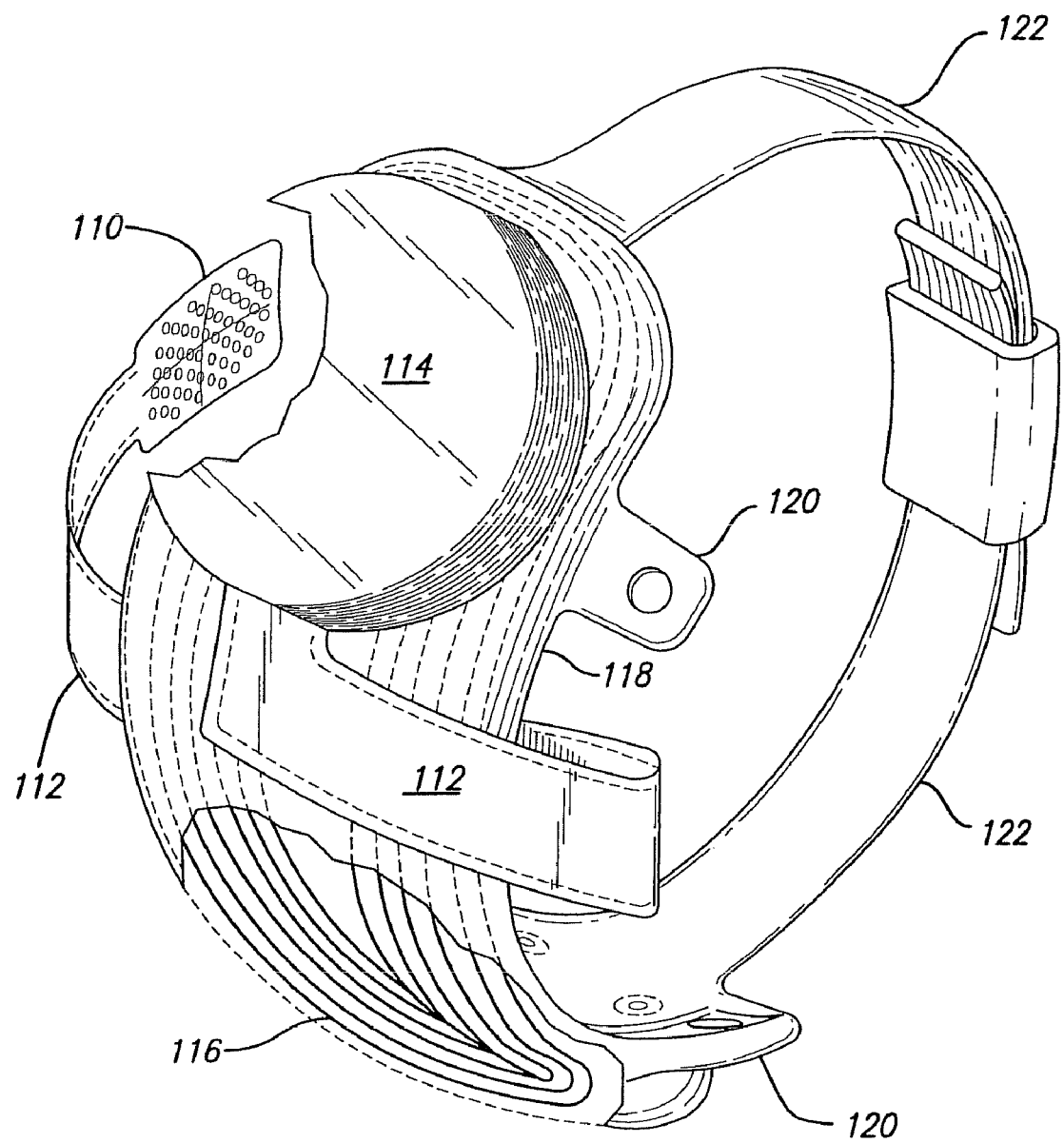
FIG. 4 is a perspective view of the implanted portion of the preferred visual prosthesis.

FIG. 4 shows a perspective view of the implanted portion of the preferred retinal prosthesis. An electrode array 110 is mounted by a retinal tack or similar means to the epiretinal surface. The electrode array 110 is electrically coupled by a cable 112, which pierces the sclera and is electrically coupled to an electronics package 114, external to the sclera.

The electronics package 114 is electrically coupled to a secondary inductive coil 116. Preferably the secondary inductive coil 116 is made from wound wire. Alternatively, the secondary inductive coil may be made from a thin film polymer sandwich with wire traces deposited between layers of thin film polymer. The electronics package 114 and secondary inductive coil 116 are held together by a molded body 118. The molded body 18 may also include suture tabs 120. The molded body narrows to form a strap 122 which surrounds the sclera and holds the molded body 118, secondary inductive coil 116, and electronics package 114 in place. The molded body 118, suture tabs 120 and strap 122 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 116 and molded body 118 are preferably oval shaped. A strap can better support an oval shaped coil.

It should be noted that the entire implant is attached to and supported by the sclera. An eye moves constantly. The eye moves to scan a scene and also has a jitter motion to prevent image stabilization. Even though such motion is useless in the blind, it often continues long after a person has lost their sight. It is an advantage of the present design, that the entire implanted portion of the prosthesis is attached to and supported by the sclera. By placing the device under the rectus muscles with the electronics package in an area of fatty issue between the rectus muscles, eye motion does not cause any flexing which might fatigue, and eventually damage, the device.

Figure 5:
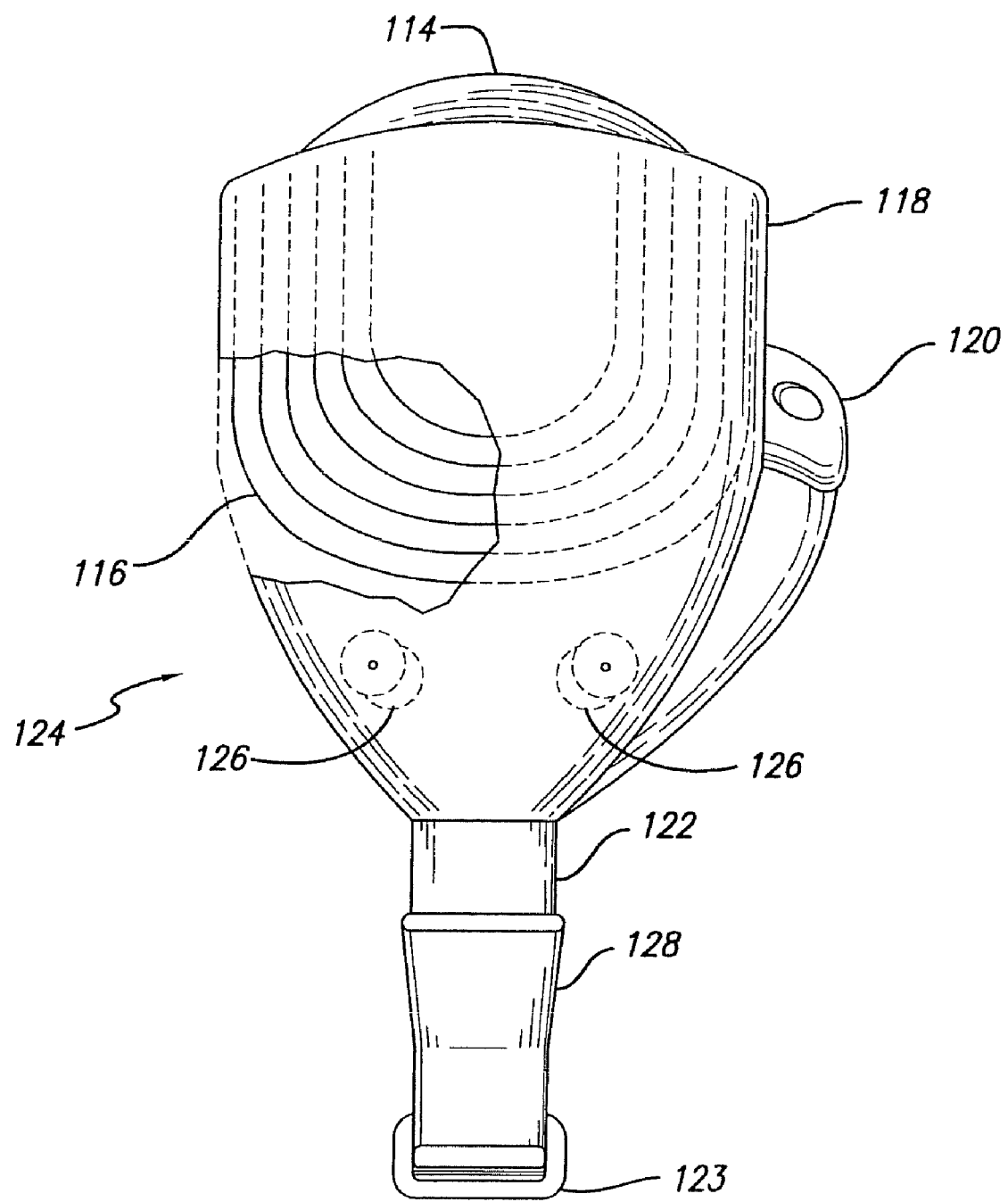
FIG. 5 is a side view of the implanted portion of the preferred visual prosthesis showing the fan tail in more detail.

FIG. 5 shows a side view of the implanted portion of the retinal prosthesis, in particular, emphasizing the fan tail 124. When implanting the retinal prosthesis, it is necessary to pass the strap 122 under the eye muscles to surround the sclera. The secondary inductive coil 116 and molded body 118 must also follow the strap under the lateral rectus muscle on the side of the sclera. The implanted portion of the retinal prosthesis is very delicate. It is easy to tear the molded body 118 or break wires in the secondary inductive coil 116. In order to allow the molded body 18 to slide smoothly under the lateral rectus muscle, the molded body is shaped in the form of a fan tail 24 on the end opposite the electronics package 114.

Accordingly, what has been shown is an improved method of making a neural prosthesis and an improved method of stimulating neural tissue. While the invention has been described by means of specific embodiments and applications thereof, it is understood that numerous modifications and variations could be made thereto by those skilled in the art without departing from the spirit and scope of the invention. In particular, the preferred embodiment describes a retinal prosthesis for artificial vision. It should be obvious to one skilled in the art that the invention has broad applicability to other types of neural stimulation. It is therefore to be understood that within the scope of the claims, the invention may be practiced otherwise than as specifically described herein.

The invention claimed is:

1. A neural stimulator comprising:
   means for providing a first supra-threshold pulse on a stimulating electrode suitable to contact neural tissue;
   means for providing a first sub-threshold pulse on an electrode near said stimulating electrode, said electrode near said stimulating electrode being suitable to contact neural tissue;
   means for providing a second supra-threshold pulse on said stimulating electrode; and
   means for providing a second sub-threshold pulse on said electrode near said stimulating electrode,
   wherein the first sub-threshold pulse and the first supra-threshold pulse are charge balanced pulses.

2. The neural stimulator according to claim 1, further comprising
   means for determining a desired stimulation level;

means for controlling the duration of said first and second sub-threshold pulses according to said desired stimulation level; and means for controlling the amplitude of said first and second supra-threshold pulses according to said desired stimulation level.

3. The neural stimulator according to claim 1, wherein said first sub-threshold pulse is anodic and said first supra-threshold pulse is cathodic.

4. The neural stimulator according to claim 1, wherein said neural stimulator is suitable to stimulate visual neurons to create the perception of a visual image.

5. The neural stimulator according to claim 4, wherein said desired stimulation level is a desired brightness.

6. The neural stimulator according to claim 4, wherein said visual neurons are retinal neurons.

7. The neural stimulator according to claim 1, wherein said first sub-threshold pulse is cathodic and said first supra-threshold pulse is anodic.

8. The neural stimulator of claim 1, wherein the first sub-threshold pulse starts simultaneously with the first supra-threshold pulse and the second sub-threshold pulse starts simultaneously with the second supra-threshold pulse.

9. The neural simulator of claim 1, wherein the second sub-threshold pulse and the second supra-threshold pulse are charge balanced pulses.

10. The neural simulator of claim 1, wherein the second sub-threshold pulse is opposite and equal to the first sub-threshold pulse and the second supra-threshold pulse is opposite and equal to the first supra-threshold pulse.

11. The neural simulator of claim 1, wherein:

the first supra-threshold pulse is provided during a first supra-threshold pulse time period;

the first sub-threshold pulse is provided during a first sub-threshold pulse time period overlapping with the first supra-threshold pulse time period;

the second supra-threshold pulse is provided during a second supra-threshold pulse time period;

the second sub-threshold pulse is provided during a second sub-threshold pulse time period overlapping with the second supra-threshold pulse time period;

the first supra-threshold pulse time period is separated in time from the second supra-threshold pulse time period; and the first sub-threshold pulse time period is separated in time from the second sub-threshold pulse time period.

* * * * *